United States Patent
Davis

(10) Patent No.: US 12,403,244 B2
(45) Date of Patent: Sep. 2, 2025

(54) SYRINGE INFUSION PUMP

(71) Applicant: Benjamin Martin Davis, Woodstock, GA (US)

(72) Inventor: Benjamin Martin Davis, Woodstock, GA (US)

(73) Assignee: ADAVATION LLC, Woodstock, GA (US)

( * ) Notice: Subject to any disclaimer, the term of this patent is extended or adjusted under 35 U.S.C. 154(b) by 0 days.

(21) Appl. No.: 18/647,321

(22) Filed: Apr. 26, 2024

(65) Prior Publication Data
US 2024/0382670 A1 Nov. 21, 2024

Related U.S. Application Data

(60) Provisional application No. 63/503,162, filed on May 18, 2023.

(51) Int. Cl.
*A61M 5/142* (2006.01)

(52) U.S. Cl.
CPC .......... *A61M 5/14212* (2013.01); *A61M 2205/3327* (2013.01); *A61M 2205/3569* (2013.01); *A61M 2205/6018* (2013.01); *A61M 2205/6072* (2013.01)

(58) Field of Classification Search
CPC ...... A61M 2205/60; A61M 2205/6018; A61M 2205/6063; A61M 2205/6072; A61M 2205/6045; A61M 2205/6036; A61M 2205/3569; A61M 5/14212
See application file for complete search history.

(56) References Cited

U.S. PATENT DOCUMENTS

| | | |
|---|---|---|
| 2,290,348 A | 7/1942 | Moule |
| 2,434,612 A | 1/1948 | Hamiel |
| 2,783,908 A | 3/1957 | Winfield |
| 3,307,752 A | 3/1967 | Anderson |
| 3,545,637 A | 12/1970 | Barr |

(Continued)

FOREIGN PATENT DOCUMENTS

| | | |
|---|---|---|
| CN | 112208932 A | 1/2021 |
| DE | 20302788 U1 | 6/2004 |

(Continued)

OTHER PUBLICATIONS

Baxa {Baxter) RAPIDFILL Connector; 1 pg; last retrieval date Jan. 13, 2023.

(Continued)

*Primary Examiner* — Bradley J Osinski
(74) *Attorney, Agent, or Firm* — Perilla Knox & Hildebrandt LLP; Stephanie Davy-Jow

(57) ABSTRACT

A syringe pump system for delivering controlled delivery of fluids from a syringe. The syringe pump system includes a keyed coupling and a motorized syringe pump. The keyed coupling includes an identifiable key piece that identifies which application or area of therapy is desired. The syringe pump includes a pump housing, a sliding key bed for receiving and reading the identifiable key piece of the keyed coupling, and a plunger actuator for actuating a plunger of the syringe. An internal software may be used to determine the correct drug or nutritional libraries and syringe specifications preprogrammed into the pump.

20 Claims, 3 Drawing Sheets

(56) References Cited

U.S. PATENT DOCUMENTS

| | | | |
|---|---|---|---|
| 3,645,262 | A | 2/1972 | Harrigan |
| 3,735,888 | A | 5/1973 | Jacko |
| 4,230,112 | A | 10/1980 | Smith |
| 4,303,071 | A | 12/1981 | Smith |
| 4,317,448 | A | 3/1982 | Smith |
| 4,493,348 | A | 1/1985 | Lemmons |
| 4,508,236 | A | 4/1985 | Keilman et al. |
| 4,515,752 | A | 5/1985 | Miramanda |
| 4,573,506 | A | 3/1986 | Paoletti |
| 4,685,173 | A | 8/1987 | Pavur |
| 4,838,857 | A * | 6/1989 | Strowe .............. A61M 5/1456 604/67 |
| 4,883,483 | A | 11/1989 | Lindmayer |
| 4,944,736 | A | 7/1990 | Holtz |
| 4,978,335 | A * | 12/1990 | Arthur, III .......... A61M 5/1456 D24/111 |
| 5,060,812 | A | 10/1991 | Ogle, II |
| 5,088,612 | A | 2/1992 | Storar et al. |
| 5,232,109 | A | 8/1993 | Tirrell et al. |
| 5,238,130 | A | 8/1993 | Marques et al. |
| 5,356,406 | A | 10/1994 | Schraga |
| 5,429,256 | A | 7/1995 | Kestenbaum |
| 5,454,409 | A | 10/1995 | McAffer et al. |
| 5,454,805 | A | 10/1995 | Brony |
| 5,484,070 | A | 1/1996 | Graham |
| 5,573,525 | A | 11/1996 | Watson et al. |
| 5,598,939 | A | 2/1997 | Watson et al. |
| 5,620,434 | A | 4/1997 | Brony |
| 5,688,254 | A | 11/1997 | Lopez et al. |
| D398,060 | S | 9/1998 | Brown |
| 5,902,298 | A | 5/1999 | Niedospial, Jr. et al. |
| 5,921,419 | A | 7/1999 | Niedospial, Jr. et al. |
| 5,931,828 | A | 8/1999 | Durkee |
| 5,971,181 | A | 10/1999 | Niedospial, Jr. et al. |
| 6,056,135 | A | 5/2000 | Widman |
| D528,910 | S | 9/2006 | Kingsley |
| D530,200 | S | 10/2006 | Kingsley |
| 7,128,228 | B2 | 10/2006 | Collins |
| 7,681,750 | B2 | 3/2010 | Jackel |
| 7,717,281 | B2 | 5/2010 | Baudin |
| D627,899 | S | 11/2010 | Cofie |
| 7,832,581 | B2 | 11/2010 | Van Cromvoirt |
| D630,732 | S | 1/2011 | Lev et al. |
| 7,985,205 | B2 | 7/2011 | Adams |
| D644,618 | S | 9/2011 | Morihira |
| 8,100,854 | B2 | 1/2012 | Vogelin et al. |
| D674,277 | S | 1/2013 | Hanson et al. |
| 8,459,312 | B2 | 6/2013 | Manera et al. |
| 8,464,882 | B2 | 6/2013 | Tirosh |
| D686,339 | S | 7/2013 | Shima et al. |
| 8,551,068 | B2 | 10/2013 | Kyle et al. |
| D693,923 | S | 11/2013 | Hernandez et al. |
| D706,135 | S | 6/2014 | Hutchison et al. |
| 8,758,322 | B2 | 6/2014 | McCoy et al. |
| D714,142 | S | 9/2014 | Hojo |
| D716,636 | S | 11/2014 | McDonald |
| D723,181 | S | 2/2015 | Kawamura |
| 8,950,608 | B2 | 2/2015 | DeJong et al. |
| D725,284 | S | 3/2015 | Karlsson et al. |
| 8,967,405 | B2 | 3/2015 | Morrone |
| D731,065 | S | 6/2015 | Winter |
| D737,962 | S | 9/2015 | Schultz |
| 9,126,029 | B2 | 9/2015 | Fangrow et al. |
| 9,156,569 | B2 | 10/2015 | Vassallo et al. |
| 9,296,531 | B2 | 3/2016 | Luzbetak et al. |
| D756,200 | S | 5/2016 | McDonald |
| 9,345,639 | B2 | 5/2016 | Ferrara |
| 9,433,562 | B2 | 9/2016 | Ingram et al. |
| 9,968,737 | B2 * | 5/2018 | Pananen .............. A61M 5/162 |
| 10,857,068 | B2 | 12/2020 | Davis et al. |
| 11,166,876 | B2 | 11/2021 | Davis et al. |
| 11,903,902 | B2 | 2/2024 | Davis |
| 2005/0065767 | A1 | 3/2005 | Arnstein et al. |
| 2005/0087127 | A1 | 4/2005 | Yun et al. |
| 2005/0258125 | A1 | 11/2005 | Kiehne |
| 2006/0217679 | A1 | 9/2006 | Hanly et al. |
| 2008/0015539 | A1 | 1/2008 | Pieroni et al. |
| 2009/0068987 | A1 | 3/2009 | O'neil et al. |
| 2009/0230075 | A1 | 9/2009 | Springer |
| 2009/0321611 | A1 | 12/2009 | Moberg |
| 2010/0160861 | A1 * | 6/2010 | Causey, III ....... A61M 5/14566 604/131 |
| 2010/0327010 | A1 | 12/2010 | Manera et al. |
| 2011/0054436 | A1 | 3/2011 | Griffis, III et al. |
| 2012/0103470 | A1 | 5/2012 | Terwilliger et al. |
| 2012/0104054 | A1 | 5/2012 | Terwilliger et al. |
| 2012/0216909 | A1 | 8/2012 | Levy |
| 2012/0289936 | A1 | 11/2012 | Ingram et al. |
| 2013/0204202 | A1 * | 8/2013 | Trombly ........... A61M 5/16877 604/207 |
| 2014/0157731 | A1 * | 6/2014 | Perazzo ................ B65B 3/003 141/2 |
| 2014/0246616 | A1 | 9/2014 | Fangrow |
| 2014/0299568 | A1 | 10/2014 | Browne |
| 2015/0126941 | A1 | 5/2015 | Felts et al. |
| 2015/0129535 | A1 | 5/2015 | Morrone, III |
| 2015/0238387 | A1 | 8/2015 | Caetano |
| 2015/0320638 | A1 | 11/2015 | Becker et al. |
| 2016/0015601 | A1 | 1/2016 | Davidson |
| 2016/0067147 | A1 | 3/2016 | Davis et al. |
| 2016/0159635 | A1 | 6/2016 | Davis et al. |
| 2016/0217679 | A1 | 7/2016 | McNutt et al. |
| 2016/0317393 | A1 | 11/2016 | Davis et al. |
| 2016/0367439 | A1 | 12/2016 | Davis et al. |
| 2017/0014616 | A1 | 1/2017 | Davis et al. |
| 2017/0239141 | A1 | 8/2017 | Davis et al. |
| 2018/0099791 | A1 | 4/2018 | Doornbos et al. |

FOREIGN PATENT DOCUMENTS

| | | | |
|---|---|---|---|
| EP | D960616 | | 12/1999 |
| EP | 2959877 | A | 12/2015 |
| GB | 2379253 | A | 3/2003 |
| TW | M512003 | U | 11/2015 |
| WO | 1998003210 | A2 | 1/1998 |
| WO | 1998046278 | | 10/1998 |
| WO | 1999032155 | A2 | 7/1999 |
| WO | 2002085429 | | 10/2002 |
| WO | 2012024370 | A1 | 2/2012 |
| WO | 2013081699 | A2 | 6/2013 |
| WO | 2014077670 | A1 | 5/2014 |
| WO | 2015146831 | A1 | 10/2015 |
| WO | 2016040126 | A1 | 3/2016 |
| WO | 2016089869 | A1 | 6/2016 |
| WO | 2018022631 | A1 | 2/2018 |

OTHER PUBLICATIONS

Baxa Adapta-Cap Bottle Adapter; 1 pg; last retrieval date Jan. 13, 2023.

Baxter AdapIACap Bottle Adapter; 1 pg; last retrieval date Jan. 13, 2023.

BioJect Needle-Free Vial Adapter; 1 pg; last retrieval date Jan. 13, 2023.

CareFusion Universal Vented Vial Adapter; 2 pgs; 2013.

Comar Oral Syringe Bottle Adapters; 3 pgs; last retrieval date Jan. 13, 2023.

GEDSA ENFil Pharmacy Resource Guide; 3 pgs; last retrieval date Jan. 13, 2023.

Institute for Safe Medication Practices (ISMP). ISMP Guidelines for Optimizing Safe Implementation and Use of Smart Infusion Pumps. ISMP; 2020.

Medela Breastmilk Transfer Lid; 1 pg; last retrieval date Jan. 13, 2023.

Medicina ENFit Press In Adapter; 18 pgs; last retrieval date Jan. 13, 2023.

Medi-Dose EPS Press-In Bottle Adapters; 1 pg; last retrieval date Jan. 13, 2023.

Medispense Stepped Stopper; 1 pg; last retrieval date Jan. 13, 2023.

NeoMed Closed System NeoBottle; 1 pg; last retrieval date Jan. 13, 2023.

(56) References Cited

OTHER PUBLICATIONS

Non Sterile Luer Lock to Oral Slip Adapter; Health Care Logistics, Inc.; 1 pg; last retrieval date Jan. 13, 2023.
Oral Slip to Oral Slip Adapter; Health Care Logistics, Inc.; 1 pg; last retrieval date Jan. 13, 2023.
PDG—The Packaging Design Group Sealsafe Press In Bottle Adapter {PIBA); 1 pg; last retrieval date Jan. 13, 2023.
So-Med Press-In Bottle Adapters; 1 pg; last retrieval date Jan. 13, 2023.
Specialty Medical Products Coupling {Item Code SMP-SCFF); Apr. 10, 2014; 1 pg.
Sterile Luer Lock to Oral Slip Adapter; Health Care Logistics, Inc.; 1 pg; last retrieval date Jan. 13, 2023.
The Oley Foundation Resource Guide; 4 pgs; last retrieval date Jan. 13, 2023.
Total Pharmacy Supply Bottle Adapter Plug; 1 pg; last retrieval date Jan. 13, 2023.
Total Pharmacy Supply Universal Bottle Adapter; 1 pg; last retrieval date Jan. 13, 2023.
Vygon Fluid Dispensing Connector; 1 pg; last retrieval date Jan. 13, 2023.
WestPharma Vial Adapters; 2 pgs; 2014.

* cited by examiner

SYRINGE INFUSION PUMP

CROSS-REFERENCE TO RELATED APPLICATION

This application claims the benefit of U.S. Provisional Patent Application Ser. No. 63/503,162 filed May 18, 2023, the entirety of which is hereby incorporated herein by reference for all purposes.

TECHNICAL FIELD

The present invention relates generally to the field of medical syringe infusion pumps, drug delivery systems, enteral nutrition delivery systems, and medical tubing connectors that facilitate the transfer of fluids.

BACKGROUND

Various medical syringe infusion pumps are used for the delivery of intravenous medications and parenteral nutrition, enteral medications and nutrition, and neuraxial/neural medications. These areas of therapy, intravenous, enteral, and neuraxial/neural are incompatible bodily systems. Cross application/connection between these bodily systems cause wrong route administration errors that can result in patient harm and death. For this reason, best practice guidelines call for dedicated syringe infusion pumps for each of these bodily systems. These guidelines for dedicated pumps intend to reduce the risks of a wrong route delivery errors by relying on the pump's color, labeling, sensors and software, programmed syringe libraries and or programmed drug and nutrition libraries to differentiate and control the syringe/mechanism and fluid that is to be delivered to the patient. However, this is problematic for several reasons.

First, dedicated pumps for each bodily system requires a great deal of space in the acute care setting, where space is often very limited. Second, dedicated pumps for each bodily system multiplies the capital expenditure that is required. At present, instead of utilizing one syringe pump for all bodily systems, a healthcare facility will likely use two or more pumps. This multiplier is spread across the entire facility. As an example, a hospital that has ten neonatal intensive care beds would likely have a minimum of twenty to thirty syringe pumps, instead of a minimum of just ten. Another problem faced by clinicians is the learning curve, nuances, and operational differences between all these syringe pump types and the different brands and models. These differences can also create issues with data integration into the facilities' electronic medical records (EMR) systems. Despite the best practice efforts to dedicate pumps for each bodily system, and the aforementioned problems this creates, the fundamental flaw with this practice is that the risks of a tubing misconnection and or wrong route administration error is not fully minimized because the syringe and connected tubing that is installed on the pump can be placed and operated on a pump it is not intended for. Existing syringe pumps are unable to recognize the syringe connector type and its associated area of therapy that is intended for administration to the patient. Thus, the root cause of the wrong route administration errors, that is intended to be mitigated through existing means, is not adequately addressed and the risks are not fully minimized, even with the existing best practices.

It is to the provision of patient safety, practice, costs, and efficiency improvements to syringe infusion pumps that the present invention is primarily directed.

SUMMARY

In example embodiments, the present invention provides a syringe infusion pump and systems and methods for using a syringe infusion pump.

In one aspect, the present invention relates to a syringe infusion pump for intravenous, enteral, and neuraxial/neural applications. The infusion pump includes a keyway or track having a keyhole or receiver. The keyhole is configured to receive a key piece of a keyed coupler that's connected to the syringe that is to be operated by the pump. In example embodiments, the coupler portion of the keyed coupler is configured to only connect with the syringe and tubing type/application that is intended to operate with the pump. The keyhole is movable along the track so that the key piece can be aligned with the keyhole, regardless of the length of the syringe that is connected to the keyed coupler. A tube or extension set, with the same paired connector type as the syringe and its intended area of therapy, can be coupled to the opposing side of the keyed coupler for facilitating the delivery of the fluid from the syringe to the patient, for that specific and intended area of therapy. In example embodiments, analog or mechanical engagement of the key piece with the keyhole permits operation of the pump. In example embodiments, the pump will not function if the key piece is not inserted within the keyhole so as to satisfy the mechanical engagement. In other example embodiments, the key piece and keyhole (or optionally one or more components of the pump) permit wireless communication of data therebetween. In example embodiments, the key piece is wirelessly verified with the pump when it is within a certain proximity thereto, and wherein the key piece proximity must remain within a certain zone or operation threshold otherwise the pump will unpair from the key piece and require reconnection prior to operating the pump.

In example embodiments, the key piece is specific to the application type of its attached coupler, and thus the pump, which is also intended for this application, recognizes this key and therefore confirms the application type and is able to operate. Without the key the pump will not operate, and with the "incorrect" key (a key that is for an application/coupler that the pump's software is not configured for), the pump will also not operate.

In another aspect, the present invention relates to a syringe infusion pump for intravenous, enteral, and neuraxial/neural applications. The infusion pump including a coupling for connecting a syringe type (e.g., intravenous, enteral, neuraxial/neural) and its associated tubing set when the syringe is operating with the pump, the syringe coupling having an identifiable element for being at least partially received by the pump, wherein the identifiable element is configured for communicating data to the pump, and wherein the pump receives the data from the identifiable element to obtain at least the syringe type and its associated application. Optionally, the syringe volume, the contents within the syringe, and the amount to be administered to patient may also be communicated, allowing the pump adjusts its settings accordingly to safely and properly administer the contents of the syringe to the patient.

In yet another aspect, the present invention relates to a syringe infusion pump having a keyed access system that is reconfigurable based on analog or digital data obtained from an identifiable element of a syringe coupling that's connected to the syringe containing the fluids to be administered, the identifiable element being logged with data at the time of filling the syringe with the fluid, the logged data being received by the pump when the identifiable element is in close proximity to the pump.

In example embodiments, the pump can be used for intravenous, enteral, and neuraxial/neural applications. In example embodiments, the entirety of the logged data may be stored on a server or other remote hard drive, and wherein a readable code present on the identifiable element that is received by the pump instructs an operating and control system of the pump to obtain the logged data from the server to adjust its settings.

In some example embodiments, the pump may be programmed or otherwise configured to be used for a single application type. In other words, the syringe infusion pump may be configured for use with or to accept a singular set of keyed couplings (and thereby also a singular or specific set of tubes/tubing and syringes) restricted or specific for use for one application type. Accordingly, if a pump is programmed or otherwise configured for use in one specific application type and a keyed coupling that is registered or configured to be used in another application type is received in the syringe infusion pump, the syringe infusion pump would not operate. In other example embodiments, the syringe infusion pump may be programmed or otherwise configured to be used for multiple application types and areas of therapy and configured to receive and identify various keyed couplings associated with the multiple application types. In such embodiments, the syringe infusion pump software/hardware is able to identify the keyed couplings (or the identifiable element of the keyed couplings) and correctly apply the proper software profile associate with the identified keyed coupling from a directory or database of various software profiles programmed in the syringe infusion pump for various applications and areas of therapy.

In still other aspects, the present invention relates to a syringe pump-and-coupling system for connecting a syringe to a tube for delivering contents of a syringe to a patient in a precise and controlled manner. The syringe pump-and-coupling system comprises a syringe pump and a keyed coupling. The keyed coupling comprises an identifiable element to be at least partially received by the syringe pump. The identifiable element is configured to communicate data to the syringe pump and the pump is configured to receive the data from the identifiable element and adjust its settings accordingly to safely and properly administer the contents of the syringe to the patient.

In example embodiments, the identifiable element is configured to communicate to the syringe pump at least one identifying datum to the syringe pump. The identifying data may include at least a type of application associated with the syringe coupling, a type of the syringe, a volume of the syringe, an identity of the contents within the syringe, or an amount of content to be administered to patient, or any combination thereof. Alternatively or additionally, the identifying data may be any other information or data useful to deliver contents of the syringe in a more precise and/or controlled manner. In example embodiments, the identifiable element may be specific to the application type of its attached syringe coupling.

In some example embodiments, the identifiable element may be an array of holes. Optionally, the identifiable element may be a barcode. Still optionally, the identifiable element may be a radio frequency chip.

In example embodiments, the syringe pump comprises a housing and a key bed configured to receive a portion of the keyed coupling and slidably secured to the housing. Additionally, the syringe pump may further comprise a motorized syringe plunger actuator configured to actuate a plunger of the syringe to dispense the contents of the syringe. Still additionally, the syringe pump may further comprise a clamp and a syringe bed for securing the syringe and the clamp may comprise one or more sensors to measure the diameter of the syringe.

In example embodiments, the syringe coupling comprises a first coupler for connecting to a nozzle of the syringe, a second coupler for connecting to the tube, and a key piece provided between the first and second couplers.

In yet another aspect, the present invention relates to a syringe infusion pump comprising a keyed access system that is reconfigurable based on data obtained from an identifiable element of a syringe coupling that's connected to the syringe comprising the fluids to be administered, the identifiable element being logged with data at the time of filling the syringe with the fluid, the logged data being received by the pump when the identifiable element is in close proximity to the pump. Optionally, the entirety of the logged data may be stored on a server or other remote hard drive, and wherein a readable code present on the identifiable element that is received by the pump instructs an operating and control system of the syringe to obtain the logged data from the server to adjust its settings.

These and other aspects, features and advantages of the invention will be understood with reference to the drawing figures and detailed description herein and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

DETAILED DESCRIPTION OF EXAMPLE EMBODIMENTS

Figure 1:
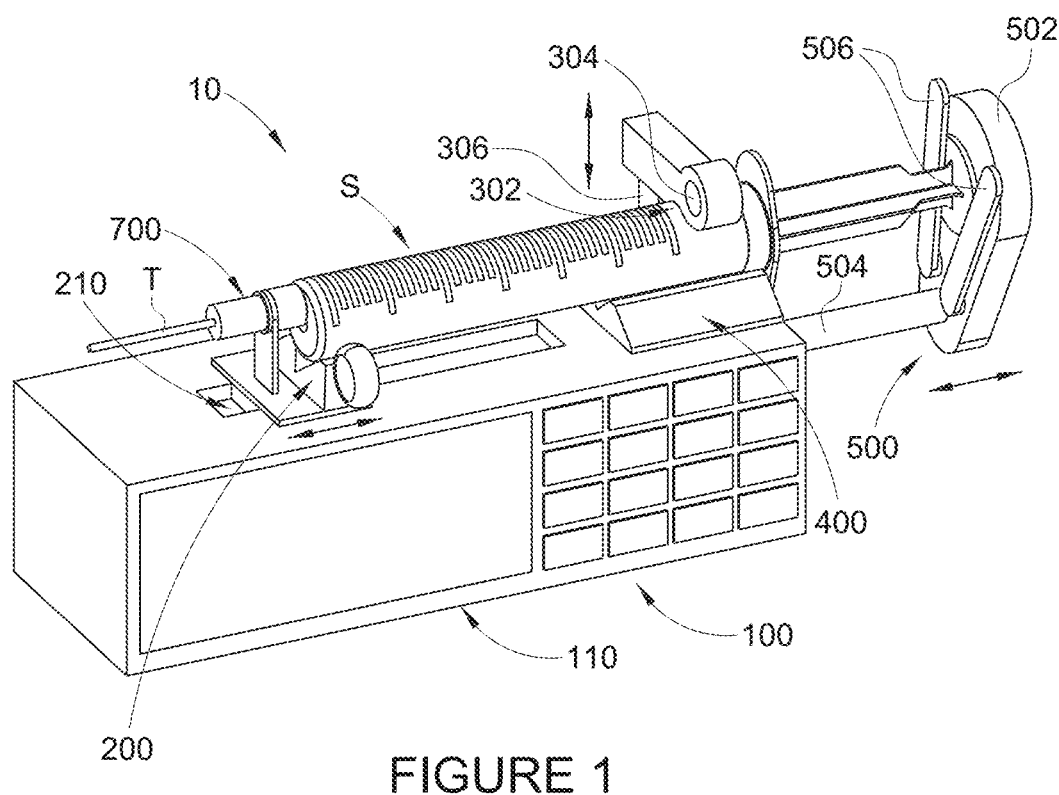
FIG. 1 shows a first perspective view of a syringe and tubing set connected to a syringe pump-and-coupling system including a syringe pump and a keyed coupling according to an example embodiment of the present invention.

The present invention may be understood more readily by reference to the following technical description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

According to example embodiments, the syringe infusion pump of the present invention may incorporate "keyed" couplings between the syringe and the medical tubing that is connected to the patient or other medical application. The pump is able to detect the keyed coupling and its software can then adjust the medication, nutrition, and syringe specification libraries and electronic medical record reporting accordingly. This keyed recognition is partially facilitated by a global international standard change that is intended to minimize small bore medical tubing misconnections. This effort is commonly defined by the International Organization for Standardization (ISO) 80369 series of standards. With this standard implementation, each bodily system is assigned a dedicated tubing connector that is mechanically incompatible with connectors that are dedicated to other bodily systems. These dedicated and mechanically incompatible small bore tubing connectors address the root cause of tubing misconnections and fluid/medication/nutrition delivery errors. In example embodiments, the present invention assigns, utilizes, and recognizes a mechanical, digital, a combination thereof, or other type of keyed coupling that is identifiable by the syringe pump. Each keyed coupling, with its dedicated connector type and its uniqueness, is able to be recognized by the infusion pump. The pump can then adjust its software, interface, and EMR data accordingly to suit the area of therapy/application that is associated with that "key". They keyed coupler prevents each syringe type from being operated on the pump under another syringe type's software settings and parameters. For example, an ISO 80369-7 (intravenous/IV/Luer) syringe and tubing set, with its dedicated connection that is only compatible with the ISO 80369-7 specific keyed coupler will only operate on the intravenous software settings and parameters of the pump. The ISO 80369-7 (intravenous/IV/Luer) syringe and tubing set could not inadvertently be operated on the pump's enteral software settings and parameters because the enteral (ISO 80369-3) keyed coupling that would be needed to access the enteral software and settings will not connect with the ISO 83969-7 syringe and tubing set.

For example according to one example embodiment the present invention comprises a syringe infusion pump for intravenous, enteral, and neuraxial/neural applications. The infusion pump comprises a keyway or track having a keyhole or receiver. The keyhole is configured to receive a key piece of a keyed coupler that's connected to the tubing set and the syringe that is to be operated by the pump. In example embodiments, the coupling portion of the keyed coupler is configured to only connect with the syringe and tubing type/application that is intended to operate with the pump. The keyhole is movable along the track so that the key piece can be engaged within the keyhole regardless of the length of the syringe that is connected to the keyed coupler. A tube or extension set can be coupled to the opposing side of the keyed coupler for facilitating the delivery of the fluid from the syringe to the patient. In example embodiments, analog or mechanical engagement of the key piece with the keyhole permits operation of the pump. In example embodiments, the pump will not function if the key piece is not inserted within the keyhole so as to satisfy the mechanical engagement. In other example embodiments, the key piece and keyhole (or optionally one or more components of the pump) permit wireless communication of data therebetween. In example embodiments, the key piece is wirelessly verified with the pump when it is within a certain proximity thereto, and wherein the key piece proximity must remain within a certain zone or operation threshold otherwise the pump will unpair from the key piece and require reconnection prior to operating the pump.

According to one example embodiment, the key piece is specific to the application type of its attached coupler, and thus the pump recognizes this key and therefore knows the application type. Without the key the pump will not operate, and with the "incorrect" key (a key that is for an application/coupler that the pump's software is not configured for), the pump will also not operate. In some example uses, facilities may only want software for one application (enteral for example, because the enteral libraries/software does not contain all the IV drug information and is therefore usually much cheaper) and if a key from another application type is tried on that pump it will not operate (providing the safety mechanism that is the "key" to the product). This would be especially useful when there are multiple pump types in the same room and the clinician needs to pick which one to use for their application.

According to another example embodiment, the present invention comprises a syringe infusion pump comprising a channel/bed (for accepting a syringe barrel) that features a sliding keyway. The sliding keyway can move forward and aft to engage with the keyed coupling as it is connectable to syringes barrels of varying lengths. The pump can detect the position of the key and can use that data to determine the syringe size/length. Historically syringe pumps utilize a barrel clamp to detect the outside diameter of the syringe and from that the pump matches the syringe (size and manufacturer) to the syringe specifications that have been installed in its software. The added ability to detect the syringe barrel length with the sliding keyway provides for more assurance that the pump is matching the physical syringe to the correct syringe specification in the software. A mismatch between the physical syringe and what the pump thinks it is detecting can result in the wrong fluid delivery rate and other errors that can result in patient harm. In situations where new syringes (syringes that are not specified in the pump software) need to be utilized with the syringe pump (perhaps an emergency situation or a situation where the programmed syringes are on backorder), the sliding keyway, in conjunction with the barrel outside diameter, which is determined by the pump's barrel clamp, can be used by the pump to calculate the syringe volume across its length and can thus determine at what rate to move the plunger armature in order to create the desired delivery/flow rate out of the syringe.

In another embodiment, the pump utilizes a detection capability (optical, light wave, laser, density scan, etc.) to detect the wall thickness and or inside diameter of the syringe and this data can then be used to ensure or increase accuracy the of the desired flow rate. In another embodiment, this thickness/inside diameter detection can also detect the opacity of the syringe. This data can be used to record/report the light protection properties of the syringe (some drugs require light protection and are therefore used in syringes with amber tinted barrels that aid in blocking light). In another embodiment, this barrel thickness/opacity sensor can also detect and record characteristics of the fluid contained in the syringe. This would be another safety mechanism. For instance, if the syringe is filled with a clear drug and it's placed on the pump and the pump is programmed to deliver a drug that is cloudy, the pump would detect this mismatch and alert the user before a medication delivery error occurs.

In another embodiment, a sensor is able to measure and record the temperature of the syringe contents. This is useful for temperature sensitive drugs and nutritionals and it can be used to alert the user if the contents are at a temperature that is outside the specified range for the drug/nutritional or at a temperature that could cause harm to the patient.

In addition to measuring and verifying/determining the syringe length/size, the sliding keyway also allows for the pump to detect when the connection between the syringe tip connector and the connector on the key are not engaged correctly. For example, for threaded connectors, the pump could use the keyway position to determine if the connectors were not fully threaded together (helpful in preventing leaks and their subsequent delivery inaccuracies; which can cause patient harm). The sliding keyway also allows for detection and use of syringes that share barrel diameter geometries but are of different volume. Historically the different syringe sizes all needed unique barrel diameters so that syringe pumps could use that uniqueness with their single measurement/detection of the syringe barrel outside diameter to determine/select the correct syringe (based on the syringe data that is loaded into the pump's software). This meant that every syringe volume needed its own outside diameter. The sliding keyway allows for the syringe pump to identify different syringe volumes, even when they have identical barrel diameters. This can allow for harmonization of some syringe sizes (for instance, a 12 mL and a 20 mL syringe may share barrel diameters and only vary in length), which can result in more efficient manufacturing, packaging, and logistics for the syringes. According to example embodiments, one or more photographs or images may be captured of the syringe over the entirety of the infusion, showing the plunger entering the barrel and the contents therein being reduced by the same amount, which can be collected and stored on a remote server or other hard drive, for example to enhance documentation and patient safety.

In example embodiments, the keyway is able to accept keys at different depths so that the syringe infusion pump can accommodate different syringe barrel diameters and different syringe tip/connector designs, e.g. concentric vs eccentric (offset). In some desired applications, the syringe pump is able to detect the engagement depth of the key in the keyway and, combining this data with the barrel diameter data that is measured with the barrel clamp armature, the pump can double check that the syringe is loaded correctly and for eccentric tip syringes it can record the tip position in the EMR. This data is useful in recording the nutrition administration parameters for breastmilk and infant formula where eccentric tip syringes are often placed in the up/12 o'clock position so that the lighter lipids (high in calories) are delivered to the patient first. The pump's ability to accept and then measure/determine the engagement depth of the key also allows for another verification that the syringe specification selected by/in the software matches with the physical syringe that is loaded onto the pump and the pump can use this data to determine if they syringe has been loaded on the pump incorrectly or if there is some other error that could affect pump/syringe operation.

In example embodiments, the pump's keyway accepts different keys that are associated with different medical applications. The pump is able to utilize the key to identify which application (area of therapy) is desired and then the software can utilize the correct drug or nutritional libraries and syringe libraries/specifications that have been programmed into the pump. Each key type is detectable, recognizable, and differentiable by the pump. In one example, this detection can occur through mechanical fitment of the key into the keyway. In another example this detection can occur by light detection through a series of holes in the key (for example light passing and detected through one hole in the key would be assigned to one application, perhaps enteral, and light passing and detected through two holes would be assigned to another application, perhaps IV). In another example, each key type is assigned a level of transparency. This transparency is detected/recognized by the pump and correct application is selected in the software. In another example, the keys utilize barcodes (linear or two-dimensional) that the pump reads upon insertion of the key into the keyway. The data encoded in the barcode allows for the pump to identify the application type (and set the software accordingly). In some instances the data encoded in the barcode can provide additional information to the pump. This data may include a myriad of useful information that can be used with the EMR, which the pump is capable of being connected to. This information may contain device data, drug data, nutritional data, patient data, etc. In other examples, the key utilizes a radio frequency (RF) chip or other wireless technology that is read by the syringe pump when the key is inserted into the keyway. This chip/wireless technology would be capable of transmitting a multitude of data types from the key to the pump. In other embodiments the key utilizes a combination of two or more of the aforementioned methods of conveying information to the pump.

In other embodiments the key is permanently affixed to the tubing that connects the syringe (that's on the pump) to the patient. This fixed connection allows for the key to convey additional information to the pump. For instance, using one of more of the aforementioned methods of key design, the key could convey tubing data (inside diameter, length, priming volume, multiport or single port, etc.) to the pump. This data could be used by the pump to detect occlusions in the tubing more accurately (based on tubing ID and syringe size, the pump would know the occlusion limits better and would be able to detect occlusions better with its force sensor that is built into its armature). This information would also allow the pump and user to know how much volume is needed to flush the tubing after medication or nutrition is delivered. In other embodiments the key design is able to convey fluid type within the same application. For instance, the key design could convey to the pump whether an enteral medication or an enteral nutrition was being delivered. In another example it could convey to the pump which type of IV application is being used (PICC, Subcutaneous, ICVC). In other embodiments, the key is freely rotatable around the tubing coupler that it is assembled to. This allows for easy screwing/fitment between the key coupler and the syringe, especially when the syringe is already installed on the pump. In another embodiment the pump is able to mark, flag, or destroy the key so that the key coupler is not able to be used again by the pump. This can be a safety mechanism for facilities that are concerned with infection prevention because it requires a new (sterile) tubing key coupler or key coupler tubing set to be used with each infusion.

In another aspect, the pump utilizes a sensor that is able to read information from the flange of the syringe. This information could be things like syringe connector type, syringe size, syringe tip offset, syringe manufacturer, syringe expiration date, plunger force requirement specifications, plunger stroke length, syringe hard height, and or other syringe information. In another embodiment this sensor configured to read a barcode, RF chip, or other wireless technology on the syringe flange that contains information on the contents of the syringe. This data and the infusion data can then be communicated by the pump to the hospitals EMR system.

In example embodiments, the pump features a vibration feature to keep syringe contents homogenized. In another embodiment, the syringe pump features a mechanism for sampling and analyzing breast milk to determine its chemical content and record that to the EMR. In another embodiment, the pump features a heating element and a cooling element to ensure that the syringe contents remain within a specified temperature range.

Example embodiments of the present invention comprise a syringe infusion pump that features a keyhole, keyway, and key coupler that work together to accommodate different syringe sizes and syringe types that are used for specific, not cross-compatible, bodily system (i.e. intravenous and enteral systems).

In example embodiments, the syringe infusion pump and systems and methods disclosed herein are preferably usable and compatible with various types of syringes and connectors or couplings, for example, of the type formatted for intravenous, enteral and neuraxial/neural applications. According to example embodiments, coupling and connectors such as those detailed in ISO 80369 and disclosed in U.S. Non-Provisional patent application Ser. No. 18/092,235 filed Dec. 31, 2022 are incorporated by reference herein and can be used with the syringes of the syringe infusion pump of the present invention.

According to example embodiments of the present invention, the syringe pumps as described herein can comprise a controller comprising a hard drive, RAM and an operating system and software, and any desired mechanical hardware or sensors or other components to provide operation. The pumps can be powered by 110V/220V electricity and/or an onboard battery may be provided. Furthermore, the controller is preferably capable of at least temporarily connecting with the internet, for example, to perform routine software updates, to receive and/or send data relative to prior or future usage. According to example embodiments, a visual screen or display may be provided, for example, to permit user interaction therewith. According to some example embodiments, one or more input selectors can be provided as desired.

According to another example embodiment, the present invention comprises a syringe infusion pump for intravenous, enteral, and neuraxial/neural applications. The infusion pump comprises a syringe coupling for connecting to the syringe when the syringe is operating with the pump, the syringe coupling having an identifiable element for being at least partially received by the pump, wherein the identifiable element is configured for communicating data to the pump, and wherein the pump receives the data from the identifiable element to obtain at least the type of application, the syringe type and volume and the contents within the syringe and the amount to be administered to patient, wherein the pump adjusting its settings accordingly to safely and properly administer the contents of the syringe to the patient.

According to another example embodiment, the present invention comprises a syringe infusion pump having a keyed access system that is reconfigurable based on data obtained from an identifiable element of a syringe coupling that's connected to the syringe containing the fluids to be administered, the identifiable element being logged with data at the time of filling the syringe with the fluid, the logged data being received by the pump when the identifiable element is in close proximity to the pump. In example embodiments, the pump can be used for intravenous, enteral, and neuraxial/neural applications. In example embodiments, the entirety of the logged data may be stored on a server or other remote hard drive, and wherein a readable code present on the identifiable element that is received by the pump instructs an operating and control system of the pump to obtain the logged data from the server to adjust its settings.

With reference now to the drawing figures, wherein like reference numbers represent corresponding parts throughout the several views, FIGS. 1-4 show a syringe pump-and-coupling system 10 according to example embodiments of the present invention. Generally, the syringe pump-and-coupling system 10 comprises a motorized syringe pump 100 for moving a plunger within a syringe S and one or more keyed couplings 700 for fluidly connecting the syringe S to one or more tubes T for delivering contents of the syringe S to a patient or subject. The keyed coupling 700 includes an identifiable element or key piece 710 configured to communicate or provide data to the syringe pump, and the syringe pump is configured to receive the data from the identifiable element 710 to obtain at least the syringe type and its associated application. Additionally or alternatively, the syringe volume, the contents within the syringe, the amount to be administered to the patient, the rate at which the contents are to be administered to the patient or subject, and/or other similar data or instructions, may also be communicated, allowing the pump to adjust its settings accordingly to administer the contents of the syringe safely and properly to a patient with minimal or no user input or intervention.

In example embodiments, the syringe pump-and-coupling system 10 includes a syringe pump 100 having a base or housing 110, a keyway (or key bed or key carrier) 200, a syringe clamp 300, a syringe bed or carrier 400, a syringe plunger actuator or armature 500, and a keyed coupling 700. The base 110 comprises a length defined between a first, proximal end and a second, distal end opposite the first, proximal end; a width defined between a first, front side or surface and a second, rear side or surface; and a height defined between a third, top side or surface and a fourth, bottom side or surface. The base 110 includes a slide track or channel 112 provided along for example its top surface. Preferably, on at least one of its sides or surfaces, or more preferably on at least one of its front or rear sides or surfaces, the base 110 also includes a visual display or screen 120 for displaying operating and configurational information and a keypad or user interface 140 enabling a user to control and operate the syringe infusion pump 100.

In example embodiments, the sliding keyway (or key bed or carrier) 200 is slidably secured or engaged in the slide track or channel 112 of the syringe pump base 110 and is configured to translate longitudinally at least partially along the length of the base. The sliding key bed 200 comprises an upper portion extending externally from the base 110 and a lower portion 210 slidably engaged to the slide track 112 and enclosed within the base 110. According to example embodiments, the key bed 200 comprises a keyhole or key receiver 202 for removably receiving the key piece 710 of the keyed coupling 700. The key bed 200 further comprises a reader or sensor (not shown) configured to read the key piece 710 when inserted in the keyhole 202 and identify, or otherwise determine, operational data and/or instructions, such as for example the syringe type and its associated application, the syringe volume, the contents within the syringe, the amount to be administered to the patient, and the rate at which the contents are to be administered to the patient or subject.

In the depicted embodiments, the syringe pump 100 is shown in a horizontal orientation. However, the syringe pump 100 may be used in any orientation as needed or desired. For example, it may be preferable in some applications or situations to orient the syringe pump 100 in a vertical orientation such that the syringe is received on the syringe pump with the syringe nozzle or tip pointing downwardly (for example, towards the support surface or floor) and the syringe plunger is moved in a downward direction during use. Similarly, in other applications or situations, the syringe pump base 110 may be in oriented in an angular orientation relative to the support surface (for example, the floor) as necessary or desired.

Figure 3:
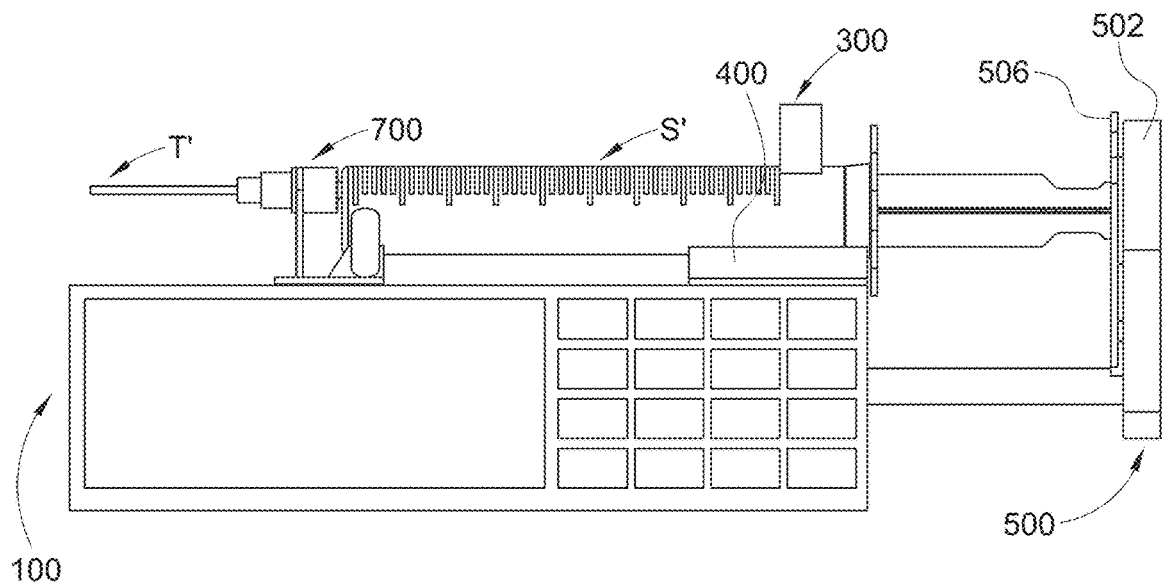
FIG. 3 shows a first side view of the syringe pump system of FIG. 1 connected to a syringe and tubing set having a first length connected thereto.
Figure 4:
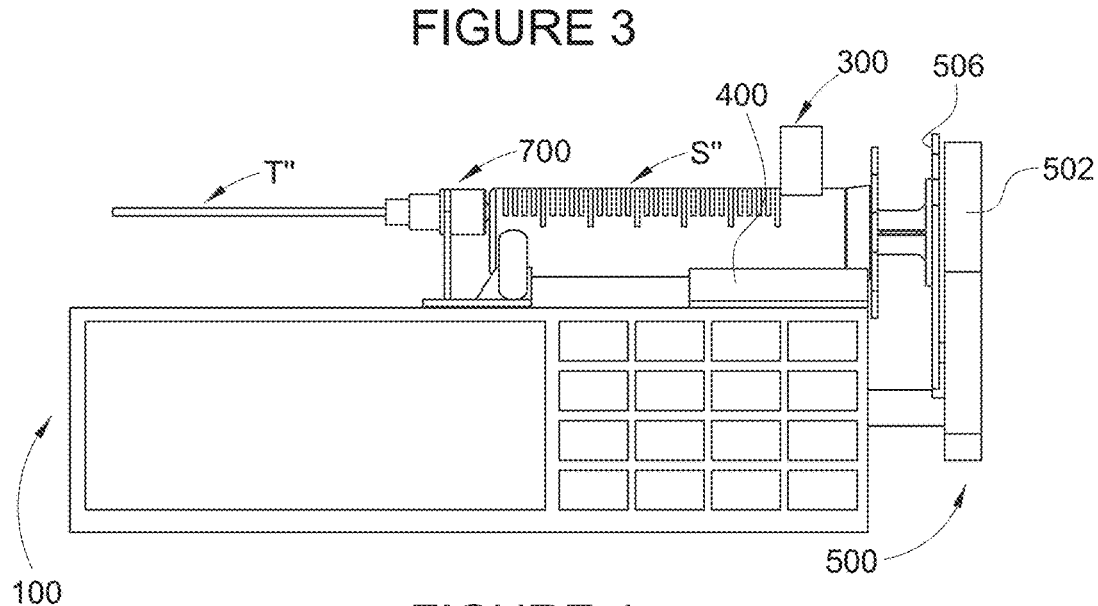
FIG. 4 shows a first side view of the syringe pump system of FIG. 1 connected to a syringe and tubing set having a second length connected thereto.

Preferably, the keyway or key bed 200 (and therefore the keyhole 202) is movable along the slide track or channel 112 so that the key piece 710 remains received within the keyhole 202 regardless of the length of the syringe S that is connected to the keyed coupling 700 (see, e.g., FIGS. 3 and 4). In other words, the sliding key bed 200 is movable forward and aft to engage with the keyed coupling 700 as it is connectable to syringe barrels of varying lengths. In example embodiments, the syringe pump 100 is configured to detect the position of the key bed 200 and can use that data to determine the syringe size/length. Historically, syringe pumps utilize a barrel clamp to detect the outside diameter of the syringe and from that the pump matches the syringe (size and manufacturer) to the syringe specifications that have been installed in its software. The added ability to detect the syringe barrel length with the sliding key bed 200 provides for more assurance that the syringe pump 100 is matching the physical syringe S to the correct syringe specification in the software. A mismatch between the physical syringe and what the syringe pump thinks it is detecting can result in the wrong fluid delivery rate and other errors that can result in patient harm. In situations where new syringes (i.e., syringes that are not specified in the pump software) need to be utilized with the syringe pump 100 (for example, in an emergency situation or a situation where the programmed syringes are on backorder), the sliding key bed 200, in conjunction with the syringe barrel's outside diameter, which may be determined by the syringe pump's barrel clamp 300, can be used by the pump 100 to calculate the syringe volume across its length and can thus determine the rate at which to move the plunger armature 500 in order to create the desired delivery/flow rate out of the syringe S.

According to some example embodiments of the present invention, the sliding key bed 200 may be configured to detect when the syringe coupler 730 is not properly connected or secured to the tip or nozzle of the syringe S. For example, for threaded connectors, the pump 100 may utilize the position of the key bed 200 to determine if the keyed coupler 700 is not fully and/or properly threaded to either the syringe S or the tube T to prevent leaks and their subsequent delivery inaccuracies, which may cause harm to the patient or subject. The sliding key bed 200 also allows for detection and use of syringes that share barrel diameter geometries but are of different volume. Historically, syringes of different sizes required unique barrel diameters so that the syringe pumps could use the barrel diameters with their single measurement or detection of the syringe barrel outer diameter to determine and select the correct syringe based on the syringe data pre-loaded into the pump's software. Accordingly, every syringe volume required a specific outer diameter. The sliding key bed or keyway 200 allows for the syringe pump 100 to identify different syringe volumes, even when they have identical barrel diameters. This can allow for harmonization of some syringe sizes (for instance, a 12 mL and a 20 mL syringe may share barrel diameters and only vary in length), which can result in more efficient manufacturing, packaging, and logistics for syringes. According to example embodiments, one or more photographs or images may be captured of the syringe over the entirety of the infusion, showing the plunger entering the barrel and the contents therein being reduced by the same amount, which can be collected and stored on a remote server or other hard drive, for example to enhance documentation and patient safety.

In example embodiments, the key bed 200 is configured to accept key pieces 710 at different depths so that the syringe pump 100 can accommodate syringes of varying diameters and tip/connector designs, e.g. concentric vs eccentric (offset). In some preferred example embodiments, the syringe pump 100 is configured to detect the engagement depth of the key piece 710 in the key hole 202 and, combining this data with the barrel diameter data that is measured with the barrel clamp armature 304, the pump 100 may be configured to verify or check that the syringe S is loaded correctly and, for eccentric tip syringes, record the tip position in the EMR. This data is useful in recording the nutrition administration parameters for breastmilk and infant formula where eccentric tip syringes are often placed in the up or 12 o'clock position so that the lighter lipids (high in calories) are delivered to the patient first. The pump's ability to accept and then measure or determine the engagement depth of the key piece 710 also allows for another verification that the syringe specification selected by or in the software matches with the physical syringe that is loaded onto the pump, which may be used to determine whether the syringe has been loaded on the pump incorrectly or if there is some other error that could affect pump/syringe operation. Additionally, the key hole 202 may be configured to releasably hold or secure the key pieces 710 when inserted in the key hole 202. For example, the key hole 202 may feature a clamp or vice to temporarily hold the key piece 710 in place during pump operation and essentially act like a second barrel clamp to help hold the nozzle end of the syringe down during use. For example, holding the nozzle end of the syringe down may help prevent the syringe from becoming dislodged from the key bed from pressure from the syringe plunger armature 500 during use.

Figure 2:
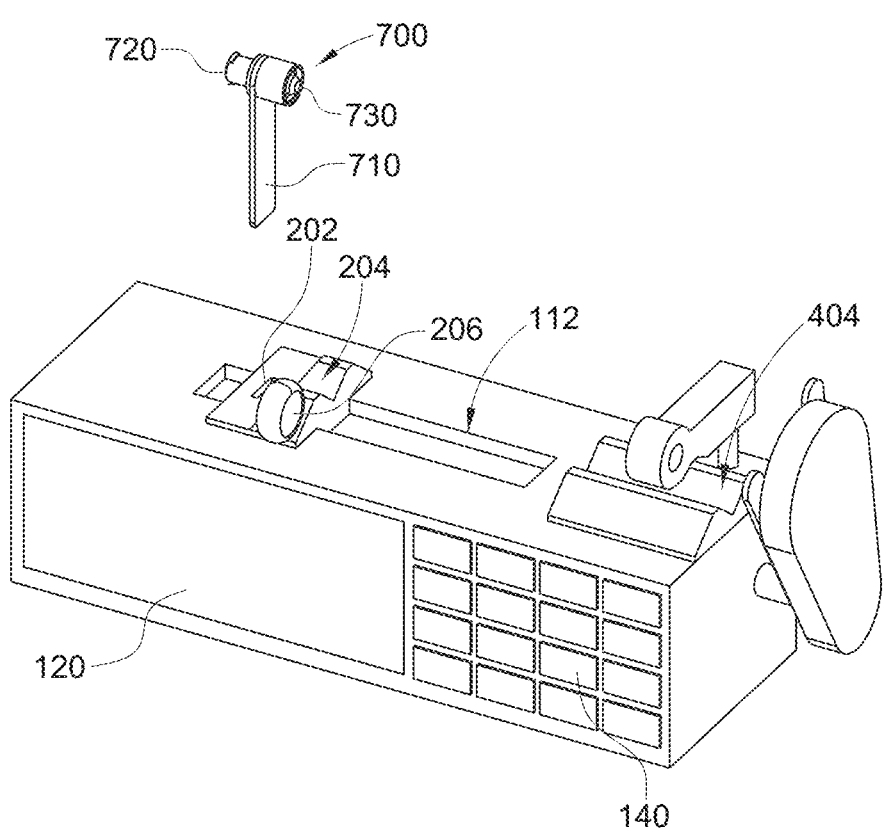
FIG. 2 shows the syringe pump-and-coupling system of FIG. 1 without the syringe and tubing set.

In example embodiments, the keyhole 202 may be configured to accept different key pieces 710 associated with different medical applications. For example, the pump 100 may be configured to utilize the key piece 710 to identify which application (or area of therapy) is desired and then an internal software may be used to determine the correct drug or nutritional libraries and syringe libraries/specifications preprogrammed into the pump. Preferably, each key type is detectable, recognizable, and differentiable by the pump 100. In example embodiments, such detection may occur through mechanical fitment of the key piece 710 in the keyhole 202. In another example embodiment, such detection may occur by light detection through an array or series of holes in the key piece as shown for example in FIGS. 6A-7B (e.g., light passing and detected through one hole in the key piece 710 may be assigned to one application, such as for example enteral, and light passing and detected through two holes may be assigned to another application, such as for example IV). In another example embodiment, each key type is assigned a level of transparency. The transparency is detected and/or recognized by the pump 100 and correct application is selected from the internal software. In another example embodiment, the key pieces 710 may utilize barcodes (e.g., linear or two-dimensional) that the pump 100 reads upon insertion of the key piece in the keyhole 202. The data encoded in the barcode may be configured to allow the pump 100 to identify the application type (and set the software accordingly). In some example embodiments, the data encoded in the barcode may provide additional information to the pump 100, including a myriad of useful information that can be used with the EMR, which the pump is capable of being connected to. Such information may contain device data, drug data, nutritional data, patient data, etc. In other example embodiments, the key piece 710 may be configured to utilize a radio frequency (RF) chip or other wireless technology that is read and/or detected by the pump 100 when the key piece 710 is inserted in the keyhole 202. Such chip/wireless technology may be capable of transmitting a multitude of data types from the key piece 202 to the pump 100. In still other example embodiments, the key piece 710 may utilize or incorporate a combination of two or more of the aforementioned methods of conveying information to the pump 100. As shown in FIG. 2, the key bed 200 further comprises a channel or groove 204 for receiving or accepting a barrel of a syringe and a handle 206 allowing for a better grip to move the key bed 200 manually as needed or desired.

In example embodiments, the syringe pump 100 further comprises a syringe bed or carrier 400 secured or otherwise provided for example on the top surface of the pump housing 110. The syringe bed 400 includes a groove or channel 404 for receiving or accepting a barrel of the syringe. Preferably, the syringe bed 400 is laterally aligned to the sliding key bed 200 such that, in example modes of use, a syringe S is supported by both the key bed 200 and the syringe bed 400.

In example embodiments, the syringe pump 100 further comprises a syringe clamp or vice 300 for releasably securing and holding the syringe S in place for example against the syringe bed 400. As best shown in FIG. 2, the syringe clamp 300 comprises a lateral arm 304 supported by an upright support or vertical post 306. In example embodiments, the syringe clamp 300 is spring-loaded or otherwise biased towards the syringe pump housing 110 so that, in example modes of use, the syringe clamp 300 presses down, or towards the housing 110, on the syringe S to keep the syringe in place during use. In the depicted embodiments, the syringe clamp further comprises an indentation or curvature 302 to accommodate the curvature of the syringe barrel. Additionally or alternatively, placement of the syringe in the channels 204, 404 of the key and/or syringe beds 200, 400 helps minimize, or more preferably prevent, the syringe from moving laterally during use. In example embodiments, the syringe clamp 300 further comprises one or more sensors (not shown) to measure for example a diameter of the syringe barrel. For example, the syringe clamp 300, or more specifically the syringe clamp post 306, may comprise a sensor to measure the displacement of the syringe clamp 300, or more specifically the syringe clamp armature 304.

Figure 5:
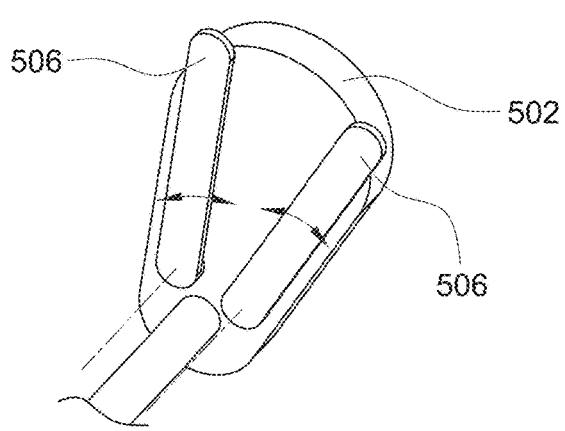
FIG. 5 is a detailed view of a plunger actuator of the syringe pump and its plunger thumb pad clamps according to example embodiments of the present invention.

In example embodiments, the syringe pump 100 further comprises a plunger actuator or armature 500 for actuating a plunger of a syringe S at a controlled rate to administer precise amounts of fluid from the syringe. As best shown in FIGS. 1 and 5, the plunger actuator 500 comprises a backstop 502 connected to a distal end of a driving arm 504. The proximal end of the driving arm, opposite its distal end, is received in the syringe pump housing 110 and is connected to and driven by a mechanical mechanism controlled by the syringe pump's internal software for precise and controlled movements. Preferably, the plunger actuator 500 further comprises an anchoring mechanism for receiving and releasably securing a flanged free end of the syringe plunger to prevent unintended movement, vibration, or dislodgement of the flanged free end of the syringe plunger during use. In the depicted example embodiment, the plunger actuator 500 includes a pair of pivoting or rotating prongs 506, as best shown in FIG. 5. The prongs are rotatable to accommodate plungers of various sizes and shapes. For example, the prongs 506 may be rotated towards one another to form a narrower opening or gap between the prongs to accept a smaller plunger end. Alternatively, the prongs 506 may be rotated away from one another to form a wider opening or gap between the prongs to accept a larger plunger end. According to example embodiments, the flanged end of the plunger is releasably secured between the prongs 506 and the backstop 502. In some example embodiments, the plunger actuator 500 may further comprise a force sensor embedded therein or connected thereto to detect occlusions in the tubing T and/or coupling 700.

As shown in FIGS. 1 and 2, the syringe pump-and-coupling system 10 further comprises at least one coupling 700 between the syringe S and the medical tubing T that is connected to the patient or other medical application (not shown). In example embodiments, the syringe pump 100 is configured to detect the keyed coupling 700 and adjust the medication, nutrition, and syringe specification libraries and electronic medical record reporting accordingly. This keyed recognition is partially facilitated by a global international standard change that is intended to minimize small bore medical tubing misconnections. This effort is commonly defined by the International Organization for Standardization (ISO) 80369 series of standards. With this standard implementation, each bodily system is assigned a dedicated set of tubing/syringe connectors that are mechanically incompatible with connectors that are dedicated to other bodily systems. These dedicated and mechanically incompatible small bore tubing connectors address the root cause of tubing misconnections and fluid/medication/nutrition delivery errors.

Figure 6A:
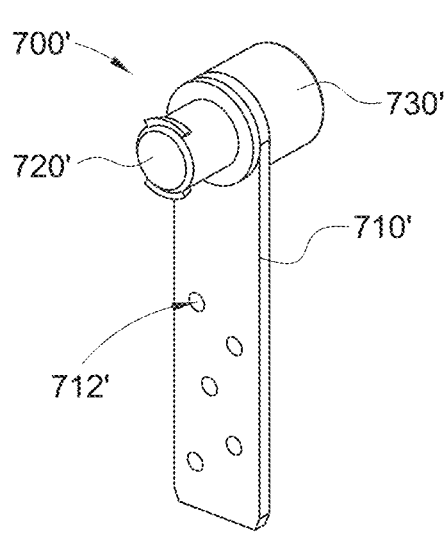
FIGS. 6A and 6B show perspective views of a first keyed coupling according to example embodiments of the present invention.
Figure 6B:
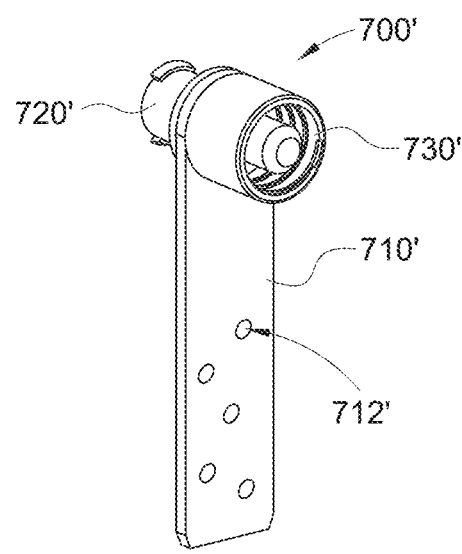
Figure 7A:
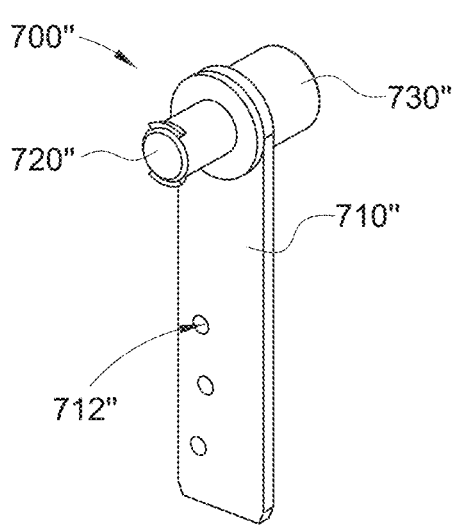
FIGS. 7A and 7B show perspective views of a second keyed coupling according to example embodiments of the present invention.
Figure 7B:
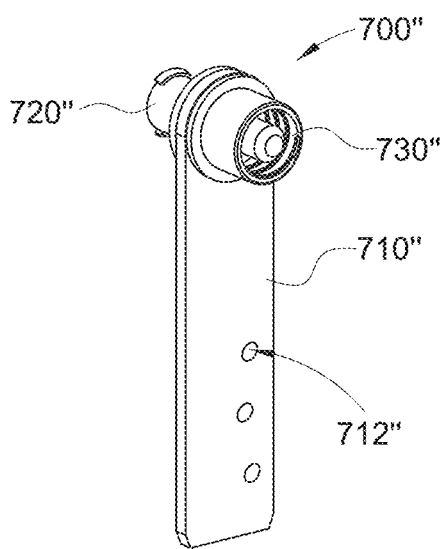

In example embodiments, the keyed coupling 700 comprises a tube coupler 720 for releasably connecting to for example a tubing T at its first, proximal end and a syringe coupler 730 for releasably connecting to for example a nozzle or tip of a syringe S at its second, distal end. In the depicted embodiments, the couplers are shown as threaded connectors; however, other suitable types of connectors may be used as desired or required by application. In example embodiments, a key piece 710 is provided between the tube and syringe couplers 720, 730. The key piece 710 may be configured to rotate freely or be rotationally affixed relative to the couplers 720, 730, the syringe pump 100 assigns, utilizes, and recognizes a mechanical, digital, other types of keyed coupling or any combination thereof that is identifiable by the syringe pump. Each keyed coupling 700, with its unique identifiable key piece 710 or identifiable element 712, is recognizable by the syringe pump 100, which allows the syringe pump 100 to adjust its software, interface, and EMR data accordingly to suit the area of therapy/application that is associated with the key piece or identifiable element. The keyed coupling 700 prevents each syringe type from being operated on the pump under another syringe type's software settings and parameters. Preferably, the syringe coupler 730 and tube coupler 720 of the keyed coupling 700 are configured to only connect with the syringe and tubing type/application that is intended to operate with the syringe pump. For example, FIGS. 6A and 6B show a keyed coupling 700' configured for use a syringe S' and tubing T' of a first type/application. Accordingly, the keyed coupling 700' comprises an internally threaded syringe coupler 730' for connecting the keyed coupling 700' to the externally threaded tip or nozzle of syringe S' (not shown) and an externally threaded tube coupling 720' for connecting the keyed coupling 700' to an internally threaded end of tubing T' (not shown). Similarly, FIGS. 7A and 7B show a keyed coupling 700" configured for use with a syringe S" and tubing T" of a second type/application. Accordingly, the keyed coupling 700" comprises a syringe coupling 730" for connecting the keyed coupling 700" to the tip or nozzle of syringe S" and a tube coupling 720" for connecting the keyed coupling 700' to the tubing T". For example, an ISO 80369-7 (intravenous/IV/Luer) syringe, with its dedicated connection that is only compatible with the ISO 80369-7 keyed coupling will only operate on the intravenous software settings and parameters of the pump 100. Accordingly, the syringe pump-and-coupling system 10 could not inadvertently be operated on the syringe pump's enteral software settings and parameters because the enteral (ISO 80369-3) keyed coupling will not connect with the ISO 83969-7 syringe.

In other words, the key piece 710 and its unique identifiers 712 are specific to the application type of its attached tube coupling 720 and syringe coupling 730, and thus the syringe pump 100 is able to determine the application type from the key piece. Preferably, the syringe pump 100 is inoperable without the key piece 710 (i.e., analog or mechanical engagement of the key piece 710 with the keyhole 202 permits operation of the pump) or with the "incorrect" key piece (i.e., a key that is for an application/coupling that the syringe pump's software is not configured for). For example, the syringe pump 100 will not function if the key piece 710 is not inserted within the keyhole 202 so as to satisfy the mechanical engagement. In other example embodiments, the key piece 710 and keyhole 202 (or optionally one or more components of the syringe pump 10) permit wireless communication of data therebetween. In still other example embodiments, the key piece 710 is wirelessly verified with the syringe pump 100 when it is within a certain proximity thereto and, if key piece 710 does not remain within a certain zone or operation threshold to the syringe pump 100, the syringe pump 100 unpairs from the key piece 710 and requires reconnection prior to operating the syringe pump 100.

In some example embodiments, the pump may be programmed or otherwise configured to be used for a single application type. In other words, the syringe infusion pump may be configured for use with or to accept a singular set of keyed couplings (and thereby also a singular or specific set of tubes/tubing and syringes) restricted or specific for use for one application type. Accordingly, if a pump is programmed or otherwise configured for use in one specific application type and a keyed coupling that is registered or configured to be used in another application type is received in the syringe infusion pump, the syringe infusion pump would not operate. In other example embodiments, the syringe infusion pump may be programmed or otherwise configured to be used for multiple application types and areas of therapy and configured to receive and identify various keyed couplings associated with the multiple application types. In such embodiments, the syringe infusion pump software/hardware is able to identify the keyed couplings (or the identifiable element of the keyed couplings) and correctly apply the proper software profile associate with the identified keyed coupling from a directory or database of various software profiles programmed in the syringe infusion pump for various applications and areas of therapy.

Figure 8:
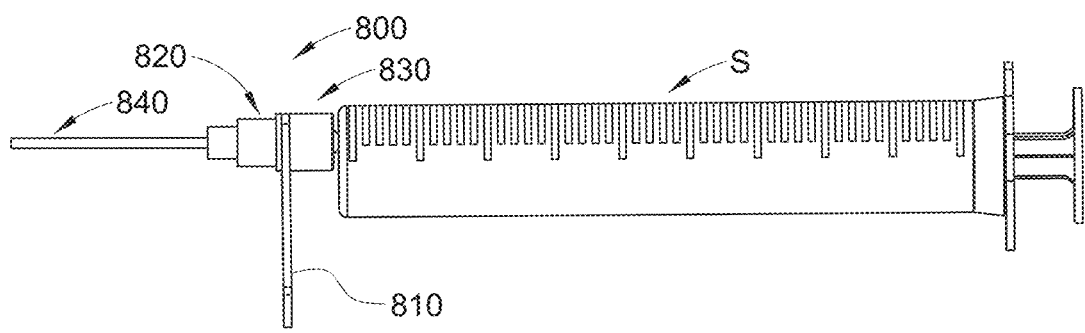
FIG. 8 shows a keyed coupling with an integrated tubing according to an example embodiment of the present invention.

In some example embodiments, the keyed coupling 800 may be permanently affixed to a tubing 840 fluidly connecting the syringe S to the patient, as shown in FIG. 8. Such fixed connection allows for the key piece 810 to convey additional information to the pump 100. For example, using one or more methods of key design described herein, the key piece 810 may be configured to convey tubing data, such as for example the inner diameter, length, priming volume, multiport or single port, and or intended delivery route (for IV applications: PICC, Subcutaneous, ICVC, etc. and for enteral applications: nasogastric, orogastric, gastrostomy, jejunostomy, etc.) to the pump. This data can be used by the pump 100 to detect occlusions in the tubing more accurately and it can also allow for the pump software control aspects like administration rates that may need to be considered for different delivery routes. For example, based on tubing ID and syringe size, the pump 100 may be configured to better detect occlusions with a force sensor built into its armature 500). The information would also allow the pump 100 and the user to determine how much volume is needed to flush the tubing T after medication or nutrition is delivered. In example embodiments, the keyed coupling 800 further comprises a syringe coupler 830 for fluidly connecting the keyed coupling 800a syringe S and a tube coupler portion 820 fluidly connecting the syringe coupler 830 to the tubing 840. Similarly, the keyed coupling may be permanently affixed or integrated to for example the tip or nozzle of the syringe rather than the tubing, and the key piece may be configured to convey syringe data, such as for example, the syringe application type, the syringe barrel dimensions, the contents of the syringe, etc.

In still other example embodiments, a syringe pump may comprise more than one base or housing 110, key bed or carrier 200, syringe clamp 300, syringe bed or carrier 400, and/or syringe plunger actuator or armature 500. For example, a syringe pump according to one example embodiment may have a singular base 110 comprising two key beds, two syringe clamps, two syringe beds, and two syringe plunger armatures, the syringe pump being generally configured to receive and operate for example two syringes for different applications or medications. The pump may be used to operate the two syringes simultaneously or one after the other.

While the invention has been described with reference to example embodiments, it will be understood by those skilled in the art that a variety of modifications, additions and deletions are within the scope of the invention, as defined by the following claims.

What is claimed is:

1. A syringe infusion pump for facilitating delivery of fluid from a syringe to a patient, the syringe infusion pump comprising a sliding key bed having a keyhole wherein the sliding key bed slides with respect to the pump, the keyhole being configured to receive a key piece of a keyed coupling, wherein the keyed coupling comprises a syringe connector at a first side and a tubing set connector on a second side, wherein the keyed coupling is configured to deliver fluid to one particular bodily system of the patient, and the keyhole being movable along a slide track such that the key piece remains received within the keyhole regardless of the length of the syringe.

2. The syringe infusion pump of claim 1, further comprising a syringe connected to the first side and a tube or extension set coupled to the second side.

3. The syringe infusion pump of claim 1, wherein analog or mechanical engagement of the key piece with the keyhole permits operation of the syringe infusion pump.

4. The syringe infusion pump of claim 1, wherein the key piece comprises an identifiable element configured to control operation of the syringe infusion pump.

5. The syringe infusion pump of claim 4, wherein the identifiable element is specific to the particular bodily system type of its attached keyed coupling, and wherein the syringe infusion pump is configured to identify the identifiable element and therefore accommodate the particular bodily system type.

6. The syringe infusion pump of claim 1, wherein syringe infusion pump is configured to wirelessly verify the key piece when it is within a certain proximity to the syringe infusion pump, and wherein syringe infusion pump is inoperable when the key piece is beyond a predetermined distance or operation threshold from the keyhole.

7. The syringe infusion pump of claim 1, wherein the keyed coupling is nonremovably connected to either the syringe at the first side or the tubing set on the second side.

8. The syringe infusion pump of claim 1, wherein the keyed coupling is movable along a depth of the keyhole such that the syringe connector is connectable to the syringe regardless of an offset of a tip of the syringe.

9. A syringe pump-and-coupling system for connecting a syringe to a tube for delivering contents of a syringe to a patient in a precise and controlled manner, the syringe pump-and-coupling system comprising a syringe pump and a keyed coupling, the keyed coupling comprising:
 a key;
 a syringe connector at a first side and a tubing set connector on a second side, wherein each of the syringe connector and the tubing set connector are connectable with only syringes and tubing systems compatible with one particular bodily system of the patient; and
 an identifiable element for being at least partially received by the syringe pump, wherein the identifiable element is configured for communicating data to the syringe pump, wherein the pump is configured to receive the data from the identifiable element and adjust its settings accordingly to safely and properly administer the contents of the syringe to said particular body system of the patient.

10. The syringe pump-and-coupling system of claim 9, wherein the identifiable element is configured to communicate to the syringe pump at least one identifying datum to the syringe pump, wherein the identifying data includes at least the particular bodily system associated with the keyed coupling, a type of the syringe, a volume of the syringe, an identity of the contents within the syringe, or an amount of content to be administered to patient.

11. The syringe pump-and-coupling system of claim 9, wherein the identifiable element is specific to the particular bodily system type of its attached keyed coupling.

12. The syringe pump-and-coupling system of claim 9, wherein the identifiable element is an array of holes.

13. The syringe pump-and-coupling system of claim 9, wherein the syringe pump comprises a housing having a sliding key bed slidably secured to the housing and configured to receive a portion of the keyed coupling.

14. The syringe pump-and-coupling system of claim 13, wherein the syringe pump further comprises a motorized syringe plunger actuator configured to actuate a plunger of the syringe to dispense the contents of the syringe.

15. The syringe pump-and-coupling system of claim 9, wherein the keyed coupling comprises a first coupler for connecting to a nozzle of the syringe, a second coupler for connecting to the tube, and a key piece provided between the first and second couplers.

16. The syringe pump-and-coupling system of claim 9, wherein a position of a tip of the syringe and a length of the syringe is communicated to the pump based on a placement of a keyhole along a sliding key bed and a depth of the key into a keyhole.

17. The syringe pump-and-coupling system of claim 9, wherein the syringe connector and the tubing set connector are compatible with syringes and tubing sets from an International Organization for Standardization (ISO) 80369-1:2018 series selected from: an ISO 80369-7:2021 intravascular syringe and tubing set, an ISO 80369-3:2016 enteral syringe and tubing set, and an ISO 80369-6:2016 neuraxial syringe and tubing set.

18. A syringe infusion pump comprising: a keyed access system reconfigurable based on data obtained from an identifiable element of a keyed coupling nonremovably connected to a tubing or a syringe comprising fluids to be administered, the syringe infusion pump comprising a sliding key bed having a keyhole wherein the sliding key bed slides with respect to the pump, the keyhole being configured to receive a key piece of the keyed coupling, wherein the syringe infusion pump is configured to selectively receive the data when the identifiable element is in close proximity to the pump.

19. The syringe infusion pump of claim 18, wherein the identifiable element is logged with data when the syringe is filled with the fluids.

20. The syringe infusion pump of claim 18, wherein the data received by the pump is selected from one or more of: a body system, body subsystem delivery route, tubing data, occlusion detection, light protection properties of the syringe, and characteristics of a fluid contained in the syringe.

* * * * *